United States Patent
Yatsui et al.

(10) Patent No.: US 6,906,515 B2
(45) Date of Patent: Jun. 14, 2005

(54) MAGNETIC RESONANCE IMAGING DEVICE AND METHOD

(75) Inventors: Yumiko Yatsui, Abiko (JP); Tetsuhiko Takahashi, Soka (JP); Hiroyuki Takeuchi, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/465,976

(22) PCT Filed: Dec. 27, 2001

(86) PCT No.: PCT/JP01/11593

§ 371 (c)(1), (2), (4) Date: Jun. 27, 2003

(87) PCT Pub. No.: WO02/053031

PCT Pub. Date: Jul. 11, 2002

(65) Prior Publication Data

US 2004/0056660 A1 Mar. 25, 2004

(30) Foreign Application Priority Data

Dec. 28, 2000 (JP) ......................................... 2000-400372
Apr. 4, 2001 (JP) ......................................... 2001-106040

(51) Int. Cl.$^7$ ............................................. G01V 3/00
(52) U.S. Cl. ........................................ 324/309; 324/307
(58) Field of Search ................................ 324/309, 307, 324/318, 322, 300, 319; 128/653; 600/410

(56) References Cited

U.S. PATENT DOCUMENTS

| | | | | | |
|---|---|---|---|---|---|
| 5,113,865 | A | * | 5/1992 | Maeda et al. | 600/410 |
| 5,134,372 | A | * | 7/1992 | Inoue | 324/309 |
| 5,627,469 | A | * | 5/1997 | Hong et al. | 324/309 |
| 6,459,922 | B1 | * | 10/2002 | Zhang | 600/410 |

\* cited by examiner

Primary Examiner—Brij Shrivastav
(74) Attorney, Agent, or Firm—Cooper & Dunham LLP

(57) ABSTRACT

When data of plural original images having different echo times are acquired to produce water/fat separated images by performing an processing operations in an MRI apparatus, a partial region of the original image data is specified and the specified region is subjected to the water/fat separation processing. Since noise components included in the specified region are fewer than those in the original image data, errors occurring due to noise components during unwrapping and other such processing operations can be reduced and image quality degradation be suppressed. Therefore, water/fat separated images having an excellent image quality can be produced. When echoes having different echo times are generated, rewind pulses are applied ahead of the readout gradient magnetic fields to equalize the polarities of the readout gradient magnetic fields. Consequently, influence of application of gradient magnetic fields on echo signals can be suppressed and the accuracy of water/fat separation can be improved.

15 Claims, 11 Drawing Sheets

(B)

(A)

Fat Image (B)

Water Image (A)

MAGNETIC RESONANCE IMAGING DEVICE AND METHOD

BACKGROUND OF THE INVENTION

The present invention relates to a magnetic resonance imaging (MRI) apparatus and a method of imaging a subject to be examined by utilizing nuclear magnetic resonance (NMR). In particular, it relates to an MRI apparatus and method of producing plural kinds of images by collecting plural NMR signals with different echo times.

Prior Art

An MRI apparatus produces images by exciting nuclear spins of atoms constituting a subject to be examined, mainly protons, with an RF magnetic field pulse, acquiring signals generated by NMR as echo signals, and performing various processing operations on the echo signals. Images varying in tissue contrast can be obtained by changing parameters such as TE, i.e., echo time from excitation of spins to generation of echo signals, repetition time TR and so forth, or by performing image processing operations. In clinical applications, there is a need for images in which MR signals from fat are suppressed, and various techniques for obtaining such images have been proposed and put to practical use.

Typical methods for obtaining a fat-suppressed image include (1) a selective excitation method using an RF frequency, (2) an inversion recovery method, and (3) a method using image processing operations.

Method (1) requires very high uniformity of the static magnetic field generated by a magnet in the space surrounding the subject to be examined. In method (2), while uniformity of the static magnetic field is not important, signals from tissue with T1 value about the same as that of fat may be suppressed together with the fat signals and the SNR becomes low as a whole.

A typical example of method of (3) is the Dixon method, which is described, for example, in "Simple Proton Spectroscopic Imaging" W. Thomas Dixon, RADIOLOGY, Vol.153, 189–194 (1984).

The Dixon method is a water/fat separation method that utilizes difference of chemical shift between the water proton and fat proton. Since the water proton and fat proton precess at different resonance frequencies $f_0 w$ and $f_0 f$, the magnetization vector of the water proton and that of the fat proton come to be oriented in different directions as time passes. When the difference in resonance frequencies between the water proton and fat proton is $\Delta f$ and $2\tau = 1/\Delta f$, the water proton and fat proton oriented in the same direction at the time of excitation become oriented in the opposite direction (180°), in the same direction (360°), ... alternately at each $\tau$.

The difference between the frequency of precession movement of fat proton and that of water protons is known to be 3.5 ppm and when the resonance frequencies of the water proton and fat proton are represented by $f_0 w$ and $f_0 f$ respectively, the difference $\Delta f$ can be expressed by the following formula.

$$\Delta f (= f_0 w - f_0 f) \sim \gamma B_0 \times 3.5 \times 10^{-6}$$

In the formula, $\gamma$ is gyromagnetic ratio and $B_0$ is static magnetic field intensity.

The Dixon method utilizes the above-mentioned fact that water proton and fat proton come to have the same phase and opposite phase alternately at every $\tau$; that is, the phase of water MR signals and that of fat MR signals become the same and opposite alternately.

The principle of the two-point Dixon method (abbreviated 2PD method hereinafter) is shown in FIG. 1. In the 2PD method, measurement (scan) using a gradient echo (GrE) sequence is carried out twice while changing TE. In FIG. 1, 101 indicates RF excitation pulse, and 102 and 103 indicate readout gradient magnetic fields. Slice gradient magnetic fields and phase encoding gradient magnetic fields are not shown in the figure. In the first scan, the echo time TE1 is set to be integral times $2\tau$ and a readout gradient magnetic field pulse 102 is applied. In the second scan, the echo time TE2 is set to be $\tau$ longer than TE1 of the first scan and a readout gradient magnetic field pulse 103 is applied.

The behavior of water proton spin (water signal) and fat proton spin (fat signal) are shown in the lower portion of FIG. 1, where the water signal is indicated by a black arrow and the fat signal by a white arrow. At the time of the first scan, the water signal 104 and the fat signal 105 are in the same phase. On the other hand, at the time of the second scan, the water signal 104 and the fat signal 105 are in opposite phases. When the intensities of water signals and fat signals in the (x,y) coordinate of images are represented by W(x,y) and F(x,y), respectively, signal S1(x,y) of the first scan and signal S2(x,y) of the second scan can be expressed by the following formulae (1) and (2), respectively.

$$S1(x,y) = W(x,y) + F(x,y) \tag{1}$$

$$S2(x,y) = W(x,y) - F(x,y) \tag{2}$$

Addition of these formulae (1) and (2), $S1(x,y)+S2(x,y)=2W(x,y)$, gives a water image and subtraction of these formulae, $S1(x,y)-S2(x,y)=2F(x,y)$, gives a fat image.

Although the GrE sequence is illustrated in FIG. 1, a spin echo (SE) sequence may be employed.

FIG. 2 shows the case where the SE sequence is employed. When the SE sequence is used, an RF excitation pulse 201 and RF inversion pulse 202 are applied at the same timing in two scans. In the first scan, a readout gradient magnetic field pulse 203 is applied and a signal is acquired at TE1. In the second scan, a readout gradient magnetic field 204 is applied and a signal is acquired at TE2, which is $\tau$ after TE1 of the first scan. Then, a water image and a fat image can be produced in the same manner as explained above.

According to the 2PD method, if the static magnetic field is not homogeneous, accurate results cannot be obtained. In MRI apparatuses, the static magnetic field generated by a magnet in the space surrounding the subject to be examined should ideally be homogeneous but it is not always homogeneous because of distortion of the magnet. In addition, non-uniformity of the static magnetic field may be produced by the subject present in the static magnetic field space due to different magnetization in the subject. Such non-uniformity of the static magnetic field in a field of view (FOV) causes change of the MR signal frequency and image degradation, such as position shift, flow artifact or the like. Further, image phase is changed by non-uniformity of the static magnetic field and a correct result cannot be obtained by complex processing operations between images. When the static magnetic field is not homogeneous, the aforementioned formulae (1) and (2) are modified as expressed by the following formulae (3) and (4).

$$S1(x,y) = (W(x,y) + F(x,y)) \exp(i\alpha(x,y)) \tag{3}$$

$$S2(x,y) = (W(x,y) - F(x,y)) \exp(i\alpha(x,y) + \alpha'(x,y)) \tag{4}$$

In the formula (4), "$\alpha(x,y)$" consists of a phase rotation component caused by non-uniformity of the static magnetic field generated during the time $2\tau \times n$ (=TE) and a phase rotation component caused by non-uniformity of the RF excitation pulse, and has the same value for echoes while depending on position. $\alpha'(x,y)$ is a phase rotation component caused by non-uniformity of the static magnetic field generated during the time $\tau$.

Thus, when the static magnetic field is not homogeneous, the non-uniformity of the static magnetic field generates phase difference between water signals of the first scan and water signals of the second scan and water signals and fat signals cannot be separated by a simple addition/subtraction.

In order to overcome the above problem, an auto-shimming technique is employed to directly correct non-uniformity of the static magnetic field in the FOV using additional coils (shim coils) or post-processing of images is performed to correct for non-uniformity of the static magnetic field. The latter method, which is a modified Dixon method including phase correction of signals using the static magnetic field distribution, is called a three Point Dixon (3PD) method. Principle of the 3PD method will be explained with reference to FIG. 3.

In the 3PD method, scan is performed three times while changing TE. The first and second scans are the same as those of the 2PD method. Here, in the first scan, TE1 for an RF exciting pulse 301 is set to be integer times $2\tau$ and a readout gradient magnetic field 302 is applied. In the second scan, TE2 is set to be $\tau$ longer than in the first scan and a readout gradient magnetic field pulse 303 is applied. In the third scan, TE3 is set to be $\tau$ longer than in the second scan ($2\tau$ longer than in the first scan) and a readout gradient magnetic field 304 is applied.

Signals measured in the first scan and in the second scan can be expressed by the above-mentioned formulae (3) and (4), and signals $S3(x,y)$ measured in the third scan can be expressed by the following formula (5).

$$S3(x,y)=(W(x,y)+F(x,y))\exp(i\alpha(x,y)+2\alpha'(x,y)) \quad (5)$$

In the first scan, the phase of a water signal 305 and that of a fat signal 306 become same, which is represented by 307, and has a value $\alpha$. In the second scan, the phase of a water signal 308 and that of a fat signal 309 are opposite and the phase of the water signal comes to have a value $\alpha+\alpha'$. In the third scan, a water signal 311 and a fat signal come to have the same phase, which has a value $\alpha+2\alpha'$. Since the water signal and the fat signal are in the same phase, the phase rotation amount due to non-uniformity of the static magnetic field can be found by calculating the phase of $S3(x,y)/S1(x,y)$ using the following formula (6).

$$arg(S3(x,y)/S1(x,y))=2\alpha'(x,y) \quad (6)$$

In the formula, arg( ) means finding of the phase in the parentheses.

Phase rotation amount $\alpha'(x,y)$ due to non-uniformity of the static magnetic field can be obtained by finding values of the above formula for every $(x,y)$. Then, the following formulae are calculated using the thus obtained $\alpha'(x,y)$.

$$S1'(x,y)=S1(x,y)\exp(-i2\alpha'(x,y)) \quad (7)$$

$$S2'(x,y)=S2(x,y)\exp(-i(2n+1)\alpha'(x,y)) \quad (8)$$

Since phase rotation amount due to non-uniformity of the static magnetic field is corrected for the thus obtained signals S1', S2', addition of the above formulae (7) and (8) gives a water image $W(x,y)$ and subtraction of the above formulae (7) and (8) gives a fat image $F(x,y)$.

$$S1'(x,y)+S2'(x,y)=2W(x,y)$$

$$S1'(x,y)-S2'(x,y)=2F(x,y)$$

Not only the GrE sequence but also the SE sequence can be used in the 3PD method. The same steps as in the SE sequence shown in FIG. 2 are performed till the end of the second scan and, in the third scan, a signal is acquired by applying a readout gradient magnetic field pulse $\tau$ later than in the second scan ($2\tau$ later than in the first scan).

The 3PD method explained above takes three times the ordinary scan time because the scan must be performed three times. In order to reduce the scan time, there has been proposed a method using a sequence where three echoes required for the Dixon method are measured at a single scan (called a single scan sequence hereinafter). In the single scan sequence, as shown in FIG. 4, after a first echo signal 402 is acquired at the same time as in the first scan shown in FIG. 3 after an RF pulse 401 is applied, the readout gradient magnetic field is reversed twice to generate echoes 403, 404 at $\tau$ and $2\tau$ after the first echo signal. That is, three echo signals having different echo times are acquired by applying a single RF exciting pulse 401.

While the GrE type single scan sequence is shown in FIG. 4, the SE type single scan sequence as shown in FIG. 5, in which the first echo signal is measured as a spin echo, can be employed. In this case, an RF inversion pulse 502 is applied at TE/2 after application of an RF exciting pulse 501 and a first echo signal 503 is acquired at TE while applying a readout gradient magnetic field Gr. Immediately thereafter, the readout gradient magnetic field is reversed twice to generate echoes 504, 505 at $\tau$ and at $2\tau$ after the first echo signal. Thus, three echo signals having different echo times are acquired by applying a single RF exciting pulse as in the GrE type.

As a method other than this type of 3PD, there is known a method in which a water/fat separated image is produced by finding phase rotation amount due to non-uniformity of the static magnetic field from two signals acquired at TE and TE+$\tau$ in the 2PD method. This 2PD method accompanied by the correction of the static magnetic field is described in "Two-Point Dixon Technique for Water-Fat Signal Decomposition with B0 Inhomogeneity Correction"; Bernard D. Cooms et al.; Magnetic Resonance in Medicine, Vol.38, 884–889(1997).

The aforementioned 2PD method (including the method with the static magnetic field correction) and the 3PD method have the following problems.

One problem is that calculation of phase rotation amount due to the static magnetic field non-uniformity in the 3PD method or 2PD method with the static magnetic field correction necessitates unwrapping processing, which requires a very long processing time.

The unwrapping processing will be explained hereinafter.

If phase has a value within a range from $-\pi$ to $+\pi$, only one value can be defined. However, if the static magnetic field is not homogeneous, the interval between TE1 and TE2 becomes large and at a position where the phase value is $-\pi$ or less, or $+\pi$ or more, the phase value is wrapped to have a value between $-\pi$ and $+\pi$. This situation is shown in FIG. 6, where abscissa is position and ordinate is phase rotation amount due to non-uniformity of the static magnetic field, and 601 represents a distribution of non-uniformity of the static magnetic field in FOV.

As shown in FIG. 6, the portion where the phase value is $+\pi$ or more is wrapped to have a value 603. Similarly, portions where the phase values are $-\pi$ or less is wrapped to have values 606, 607. This wrapping causes discontinuity of phase value (illustrated by a dotted line in the figure). Such discontinuity never occurs in an actual magnetic field and must be eliminated to obtain a smooth static magnetic field non-uniformity distribution by performing unwrapping processing. A method of unwrapping is described in the aforementioned paper and also in "Direct Calculation of Wrap-Free Phase Image"; M. Patel and X. Hu; Proceedings of Annual Meetings of the Society of Magnetic Resonance in Medicine (=SMRM), No. 721, 1993, and "Phase unwrapping in the Three-point Dixon Method for Fat Suppression MRI Imaging"; Jerzy Szumowski et al.; Radiology, Vol.192, 555–561(1994).

The unwrapping is a complicated and time consuming process since it is susceptible to noise and requires a technique of making masks for eliminating influence of noise. According to a preliminary examination conducted by the inventors, processing time of about 20 s–30 s was required to perform water/fat separation processing of 256× 256 original images using a workstation.

In addition, unwrapping or other such correction of the static magnetic field is susceptible to noise, especially noise generated at a portion where the examined subject is not present or a border between tissues in the subject. Such noise degrades the quality of whole image and makes it difficult to obtain an accurate water/fat separated image.

Further, the 3PD method requires calculation of phase rotation amount due to non-uniformity of the static magnetic field and this calculation itself takes a long time.

Owing to this problem of long image processing time, it is difficult to apply the water/fat separation technique to dynamic imaging for time-course observation of one portion of the examined subject. One conceivable clinical application of dynamic imaging is to monitor a needle inserted into a fat liver tumor using an MRI with considerable static magnetic field non-uniformity. In such a case, fat signals in the image must be suppressed in order to depict the tumor with high contrast and yet the image must be updated at the speed of one or two images per second. In dynamic imaging of coronary arteries, there is also a need to depict the surroundings of the coronary artery with high contrast compared to fat. Further, in examination of the movement function of limbs, which requires repeated scanning of the limbs while moving the joint, there is also a need for monitoring water/fat-separated images in semi-real time. However, the aforementioned 3PD method and the 2PD method with the static magnetic field correction are not capable of updating images because of their long processing time.

Another problem in the 3PD method, especially in the 3PD method using a single scan sequence, is insufficient water/fat separation. In experiments by the inventors, it was found that water and fat were not sufficiently separated by performing the 3PD processing of data acquired in a single scan sequence using an open-type MRI apparatus and that such insufficient separation is caused by a phase rotation component that cannot be eliminated by the processing operations of the formulae (3)–(7).

Specifically, only the phase rotation component ($\alpha(x,y)$), which is the same for all of echoes, and the phase rotation component ($\alpha'(x,y)$, $2\alpha'(x,y)$), which are caused by non-uniformity of the static magnetic field and proportional to time, have been considered in the formulae. However, there is another type of a phase rotation component, which is not proportional to time and has different values for the three echoes. Due to this component, water/fat separated images are not successfully obtained. Such a phase rotation component having different values for the three echoes includes one caused mainly by eddy currents generated by inversion of a readout gradient magnetic field.

The present invention was accomplished in order to solve the above-mentioned problems and an object of the present invention is therefore to provide an MRI apparatus and method for reconstructing plural images using plural images having different echo times or for obtaining a desired enhanced image by performing processing operations on a plurality of such signals, which is capable of producing water/fat separated images having a high image precision by effectively eliminating influence of noise in image-processing operations. Another object of the present invention is to provide an MRI apparatus and method capable of greatly reducing the time required for the water/fat separation processing operations and thereby performing continuous imaging (dynamic imaging) effectively. Yet another object of the present invention is to provide an MRI apparatus and method capable of eliminating influence of eddy currents which differs depending on signals having different echo times to perform an accurate processing operations between signals and thereby producing a plurality of images having an excellent image quality.

Disclosure of the Invention

An MRT apparatus according to the first embodiment of the present invention comprises means for selecting an enhanced image region to be formed by processing operations between signals for at least one image formed using plural signals having different echo times. Since the processing operations between signals are performed on a limited region to be observed, the amount of processing can be markedly reduced.

An MRI method of the present invention for obtaining water/fat-separated images by acquiring original image data of plural images having different echo times and performing processing operations on the image data, comprises the steps of specifying a partial region of the original image data for the water/fat separation processing, and performing the water/fat separation processing operations on the specified region to produce water images or fat images of the region.

According to a preferred embodiment of the above MRI method, original image data for at least two images having different echo times are acquired.

According to another preferred embodiment of the above-mentioned MRI method, a plurality of regions is specified as the partial region for water/fat separation processing.

According to another preferred embodiment of the above-mentioned MRI method, the original images are displayed on display means and the partial region for water/fat separation processing is specified using the displayed original images. The water/fat-separated image is displayed on the specified partial region of the original image, and an image that is not water-far separated is displayed on the other region.

An MRI apparatus according to the first embodiment of the present invention comprises a signal detecting unit for detecting NMR signals emitted from a subject to be examined, a signal processing unit for performing image processing of the detected signals, a display unit for displaying the processed images and a control unit for controlling operations of the signal detecting unit, signal processing unit and display unit, and produces water/fat-separated images by acquiring original data of plural images having different echo times and performing processing operations on the original data, which apparatus further comprises means for specifying one or plural regions of the original image data for performing the water/fat separation processing, wherein the signal processing unit performs the water/fat separation processing operations on the region specified by the specifying means and the display unit displays water images or fat images produced by the processing operations.

According to a preferred embodiment of the above MRI apparatus, a region of the original image obtained through a dynamic measurement is specified and only the specified region is subjected to the water/fat separation processing and displayed.

In the MRI apparatus of the first embodiment, the original images, which are not subjected to the water/fat separation processing, are displayed on the display unit and an operator determines a region that requires the water/fat separation processing. Thereafter, only data contained in the specified region is subjected to the water/fat separation processing. Such water/fat separation processing of the specified region is applied to the dynamic measurement and water/fat-separated images are displayed in real time.

According to the above-mentioned MRI apparatus, unnecessary data of the original image is not used in the processing operations of the water/fat separation processing. Thus, the amount of noise included in the separation processing can be reduced to reduce errors in phase unwrapping or other such water/fat separation processing. In addition, since the amount of data to be processed is reduced, the processing time can be shortened.

An MRI apparatus according to a second aspect of the present invention controls readout gradient magnetic fields for generating plural signals having different echo times so that all of signals are generated by applying the readout gradient magnetic fields having the same polarity.

According to the second aspect, conditions of the phase fluctuation caused by eddy currents of the readout gradient magnetic field can be equalized for plural signals acquired in the same scan, whereby processing operations using the phase difference between the signals can be performed accurately. This results in effective image separation utilizing the phase difference and production of plural kinds of images having an excellent image quality.

Specifically, the MRI apparatus according to the second aspect of the present invention, which acquires plural images having different echo times by a single scan measurement and produces images by performing processing operations, is characterized in that the polarities of readout gradient magnetic fields for reading out the echo signals having different echo times are equalized.

According to a preferred embodiment of the MRI apparatus, a rewind pulse having the polarity opposite to that of the readout gradient magnetic field is applied prior to the readout gradient magnetic field.

The present invention further provides an MRI apparatus comprising means for generating a static magnetic field in a space where a subject to be examined is placed, means for repeatedly applying an RF pulse for causing NMR in the subject, means for applying gradient magnetic fields in the directions of slice, phase encode, and readout, receiver means for detecting plural echo signals emitted from the subject, control means for controlling the aforementioned means so that plural echo signals having different echo times are generated during each repetition time of the RF pulse, a readout gradient magnetic field is applied at the time when the echo signal is generated and phase encode is changed at each repetition time, wherein the control means controls the gradient magnetic fields so that a pulse having the reversed polarity of the readout gradient magnetic field is applied ahead of the readout gradient magnetic field.

In the above-mentioned MRI apparatus, the pulse may be applied ahead of the readout gradient magnetic field for the second and subsequent echo signals in each repetition time. Alternatively, the pulse may be applied ahead of every readout gradient magnetic field for all of the echo signals.

PREFERRED EMBODIMENTS OF THE PRESENT INVENTION

Figure 1:
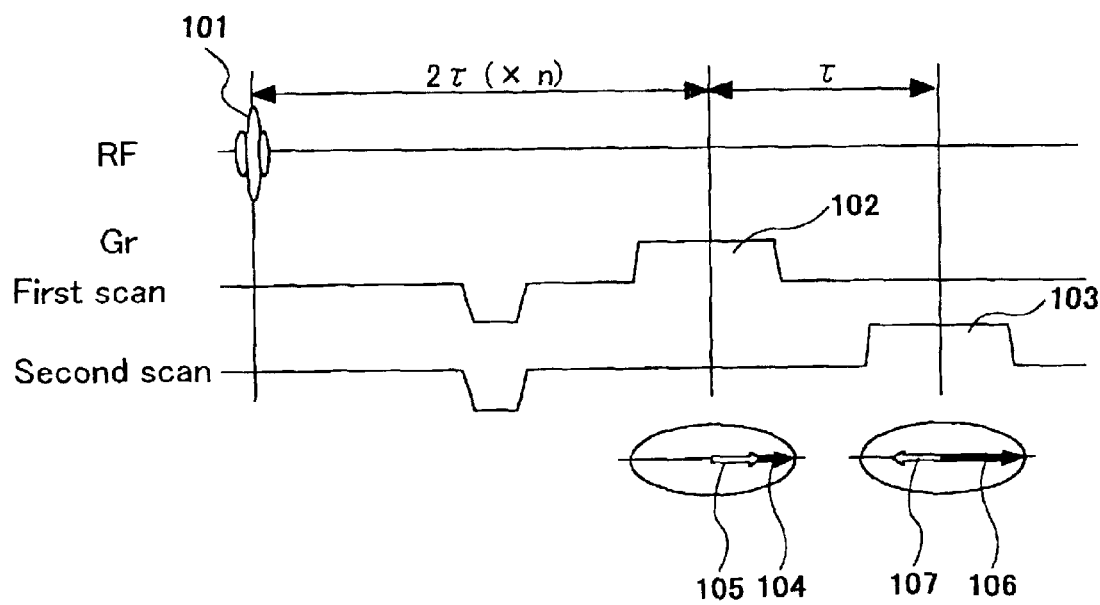
FIG. 1 is a time chart of data acquisition in the 2PD method using a GrE sequence.

Preferred embodiments of the present invention will be explained hereinafter with reference to the attached drawings.

The configuration of an MRI apparatus to which the present invention is applied will be explained using FIG. 7. The MRI apparatus comprises a magnet 702 which generates a static magnetic field in a space surrounding a patient (subject to be examined) 701, a gradient magnetic field coil 703 imparting gradient magnetic field to the space, an RF coil 704 which generates an RF magnetic field for producing NMR in atomic nuclear spins of atoms constituting tissues of the patient 701, an RF probe for detecting NMR signals emitted from the patient through NMR.

The gradient magnetic field coil 703 consists of gradient magnetic field coils of three directions X, Y, Z, each of which generates a gradient magnetic field corresponding to signals from a power supply 709. The RF coil 704 generates an RF magnetic field corresponding to signals from an RF transmitting unit 710. Signals from the RF probe 705 are detected by a signal detecting unit 706, processed by a signal processing unit 707 and transformed to image signals by calculation. Images are displayed on a display 708. The gradient magnetic field power supply 709, RF transmitting unit 710 and signal detecting unit 706 are controlled by a control unit 711. A time chart of the control is generally called a pulse sequence. Various kinds of pulse sequences corresponding to imaging methods are preinstalled in the control unit 711. A cradle 712 is provided for positioning the patient in the apparatus.

Although not illustrated in the figure, the control unit 711 is equipped with input means such as a keyboard, mouse and the like for inputting instructions to select a specific imaging method and/or various parameters. The selection of an imaging method and conditions explained hereinafter and the setting of processing operation conditions are input through the input means.

In the MRI apparatus having such a structure, the subject 701 is transported into the homogeneous static magnetic field space formed by the magnet 702, and thereafter an RF magnetic field having a frequency producing NMR in atomic nuclear spins (called simply spins hereinafter) of atoms constituting tissues of the patient is generated corresponding to signals from the RF transmitting unit 710. In this embodiment, the spins are those of the main constituent matter of the patient, i.e., protons.

Next, an imaging method according to the first embodiment of the present invention will be explained with reference to FIG. 8–FIG. 12. The imaging method executes pulse sequences according to the 2PD method or the 3PD method to obtain image data having different echo times. This process is the same as that of the conventional imaging method. However, one characteristic of this imaging method is that a one or more regions are specified for water/fat separation processing when such processing operations are performed on the image data and only water images or fat images of the specified region or regions are produced.

Figure 3:
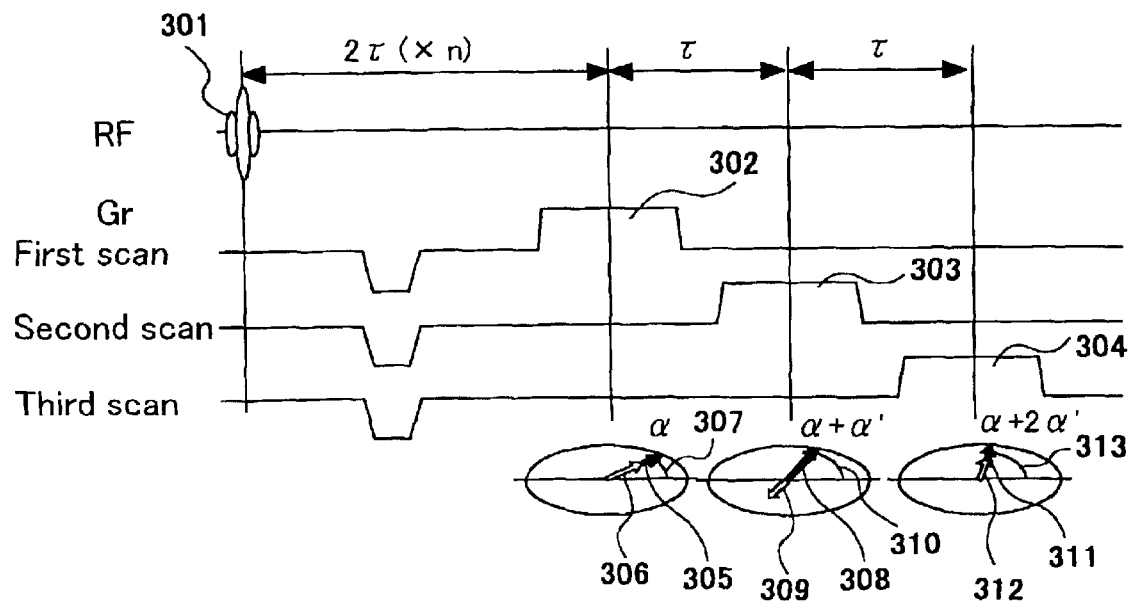
FIG. 3 is a time chart of data acquisition in the 3PD method using a GrE sequence.

One embodiment in which the imaging method of the present invention is applied to the 3PD method will be explained first. In the pulse sequence of the 3PD method, as shown in FIG. 3, a GrE sequence or SE sequence scan is conducted three times with the echo time TE set to TE1, TE2 and TE3. If the resonance frequency difference between the water and fat due to the chemical shift is $\Delta f$ and $2\tau=1/\Delta f$, the time difference between TE1 and TE2 is set toe $(2n+1)\tau$ (where n is an integer; the same applies hereinafter) and the time difference between TE1 and TE3 is set to $2n\tau$. Since signals generally attenuate with a relaxation time of T2, T2* or the like, TE2 and TE3 are set to TE1+$\tau$ and TE1+$2\tau$ respectively.

Figure 4:
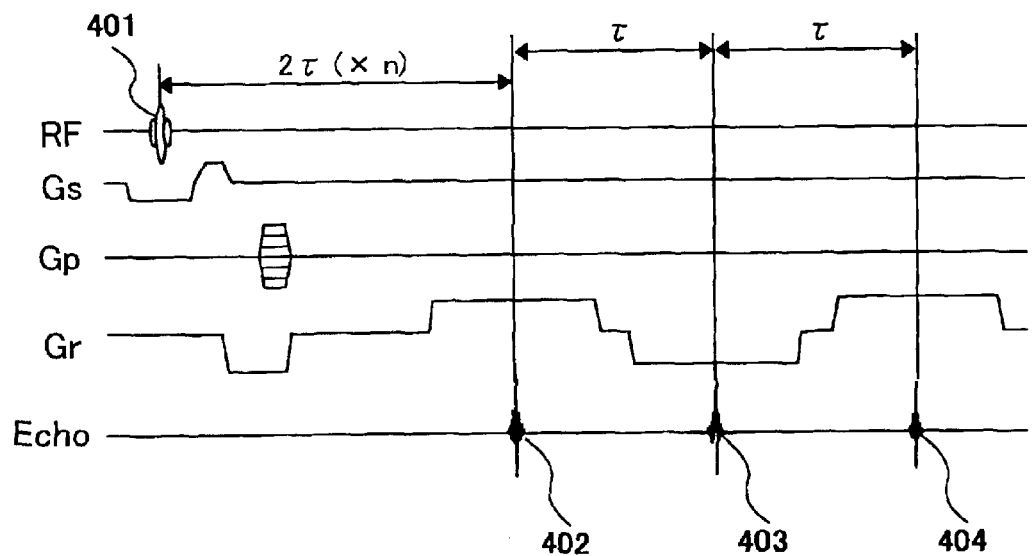
FIG. 4 shows a single-scan sequence of 3PD method using a GrE sequence.
Figure 5:
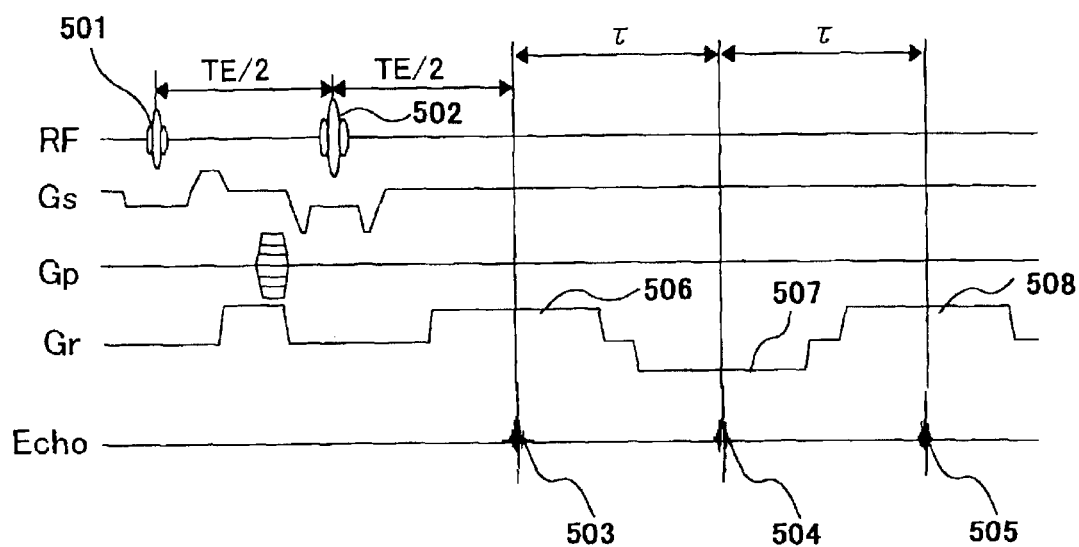
FIG. 5 shows a single-scan sequence of 3PD method using an SE sequence.

Instead of performing the scan three times, a multi-echo type SE or GrE sequence (single-scan sequence) shown in FIG. 4 or FIG. 5 may be employed where the scan is performed once to generate three echoes. Use of such a single scan sequence reduces the measurement time to one third and, therefore, larger time reduction effect can be obtained.

In such a multi-echo type sequence, the polarity of the readout gradient magnetic field is, for example, reversed alternately, as illustrated in FIG. 5 using symbols 506, 507 and 508, to obtain signals 503, 504, 505 at TE of TE1, TE2, TE3, respectively. In this case, too, the interval of reversing the readout gradient magnetic field pulse is $\tau$, and thus TE2, TE3 are set to TE1+$\tau$, TE1+$2\tau$, respectively.

In case of the three scans shown in FIG. 3, each scan is repeated while changing a phase-encoding gradient magnetic field Gp. In case of the single-scan sequence shown in FIG. 4 or FIG. 5, the single-scan sequence is repeated while changing the phase-encoding gradient magnetic field Gp. Thus, MR signals s1, s2, s3 of the required phase encode number for reconstructing of one image can be obtained.

Next, the processing operations performed on the thus obtained MR signals will be explained.

Figure 8:
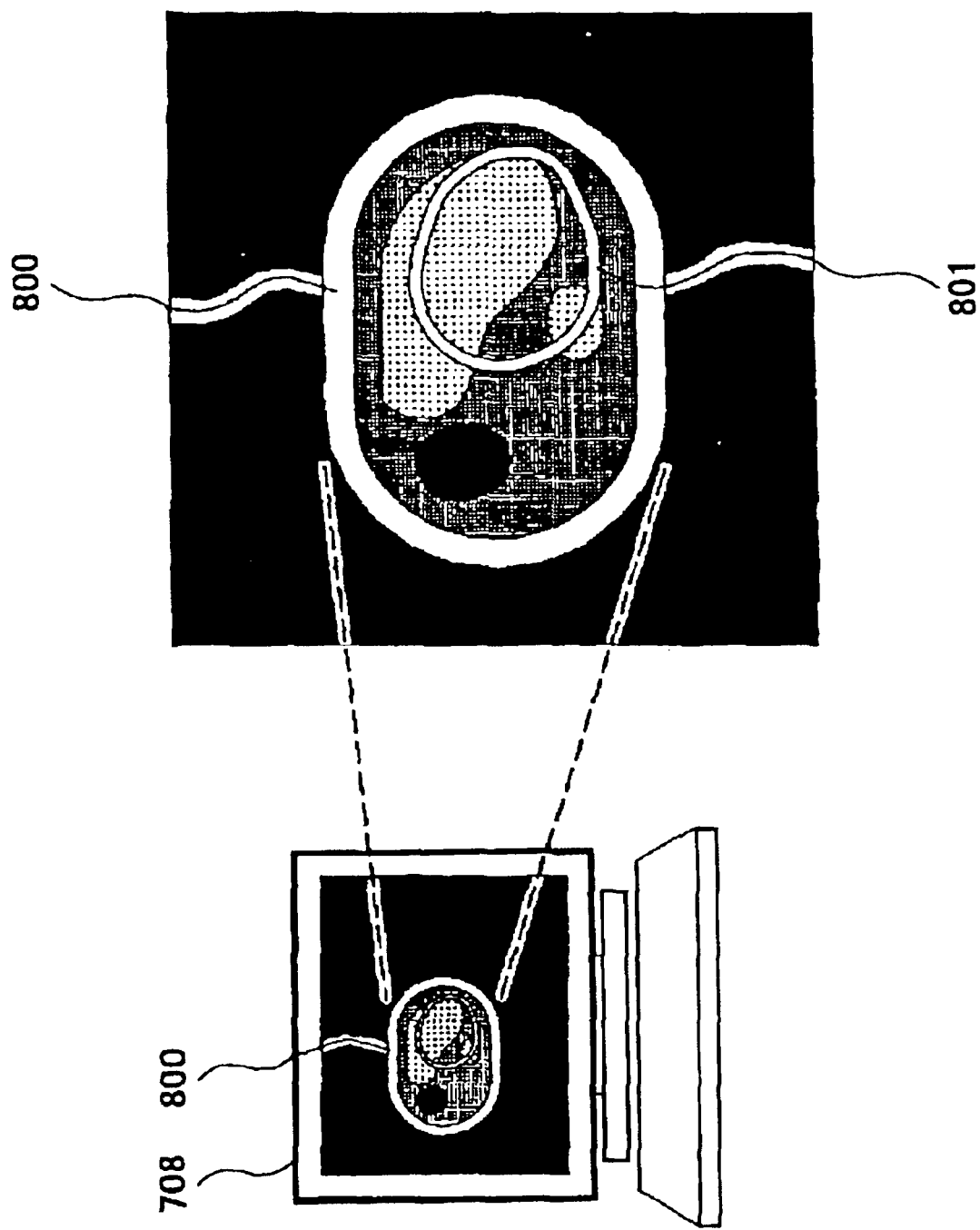
FIG. 8 is an explanatory view of region selection of an image displayed on the display according to one embodiment of the present invention.

First, Fourier transform is performed on the MR signals s1, s2 and s3 obtained by measurements of TE1, TE2 and TE3 to produce image data S1, S2 and S3. The obtained image data S1, S2 and S3 are complex data. In this embodiment, absolute value images (magnitude images) of the image data S1, S2 and S3 are displayed on the display 708. The displayed images may be any one of image data S1, S2 and S3 or any combination of them. FIG. 8 illustrates the case where only an image 800 of image data S1 is displayed.

When the image 800 is displayed on the display 708, a region on which the water/fat separation processing is to be performed (subject region) is designated on the displayed image 800. This designation can be made, for example, by drawing a border enclosing the subject region 801, which is a region constituting one part of the image 800, using an delineating tool such as a mouse pointer or a pen. Information on the thus indicated subject region (pixel address) is input into the signal processing unit 707. The number of subject regions is not limited to one but may be two or more. In such a case, information on the plural subject regions is read in the order drawn, or according the priority of the subject regions indicated separately.

Figure 9:
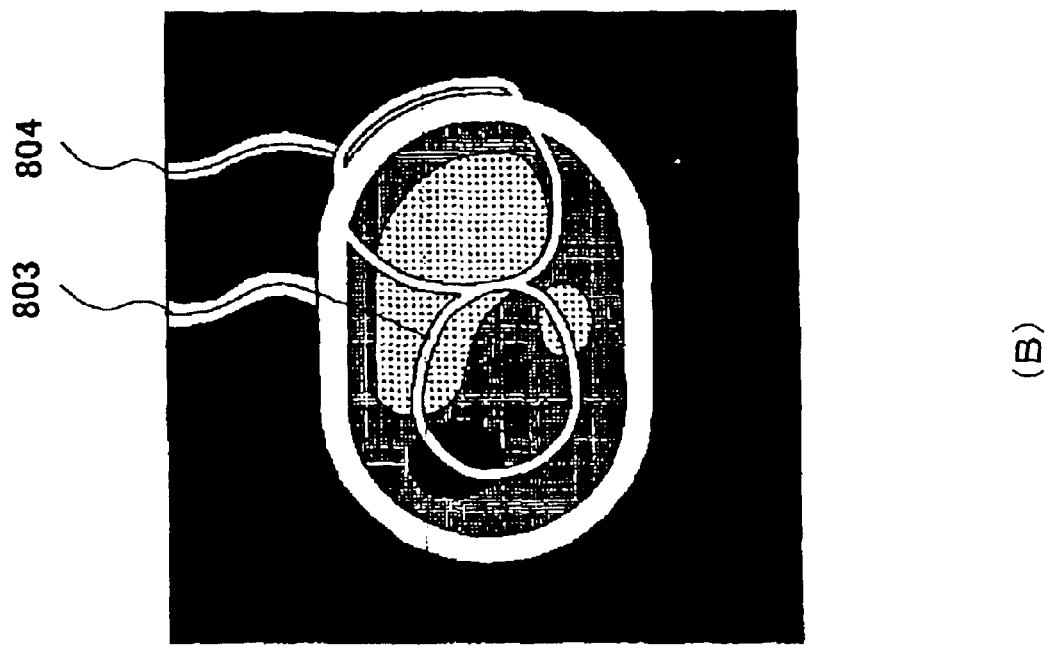
FIG. 9 illustrates a selected image displayed on the display according to one embodiment of the present invention.
Figure 9:
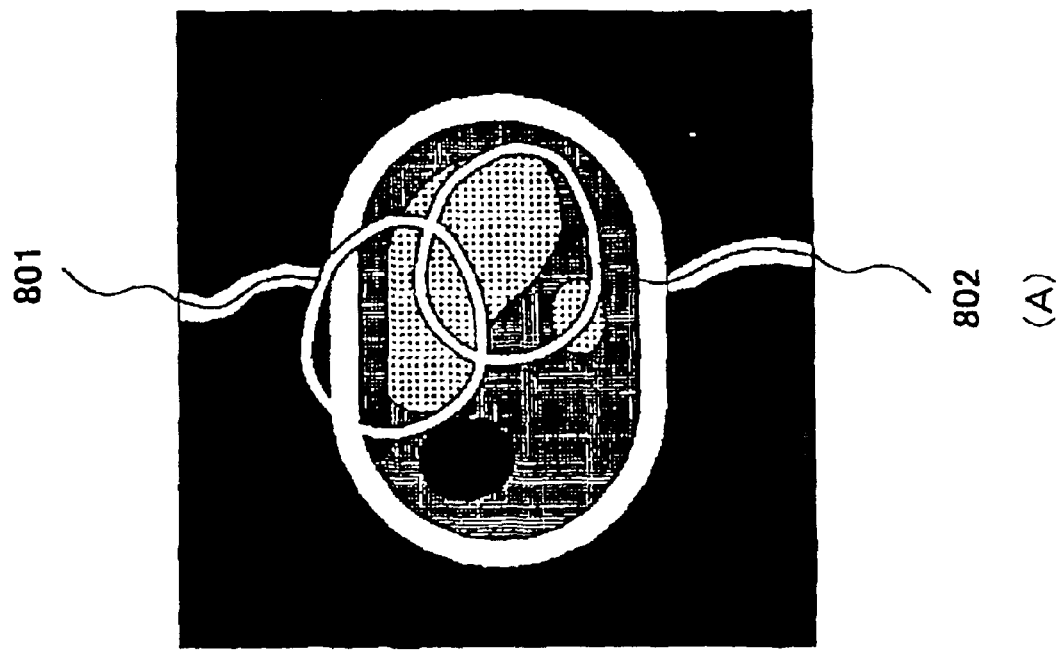

When two images (A) and (B) for image data S1 and S2 are displayed on the display 708 as shown in FIG. 9, the subject region is indicated on either of (A) and (B) in the same manner as explained above. In this case, two subject regions 801 and 802 (or 803 and 804) or plural subject regions may be indicated for one image. When plural subject regions are selected, they are read in the order drawn or according to the separately indicated priority.

While FIG. 8 and FIG. 9 illustrate that selection of the subject region is conducted by freehand drawing, a square subject region may be designated by selecting diagonally opposite corner points of the square, or a circular region can be selected. Techniques known to the art can be employed to a region in a displayed image.

Once the subject region is thus indicated, the signal processing unit 707 performs the water/fat separation processing for pixels corresponding to the indicated region. Specifically, a static magnetic field non-uniformity distribution map is formed by the following formula (6) using image data S1 and S3.

$$\arg(S3(x,y)/S1(x,y))=2\alpha'(x,y) \qquad (6)$$

Next, the unwrapping processing is performed for eliminating phase wrapping and then a phase rotation amount $\alpha'(x,y)$ due to static magnetic field non-uniformity is found by dividing the processed data by 2. Image data S1 and S2 are phase-corrected by the following formulae (7) and (8) using the phase rotation amount $\alpha'$. This phase correction is conducted only for the previously designated subject region for the water/fat separation processing.

$$S1'(x,y)=S1(x,y)\exp(-i2\alpha'(x,y)) \quad (7)$$

$$S2'(x,y)=S2(x,y)\exp(-i(2n+1)\alpha'(x,y)) \quad (8)$$

By this correction, signals S1' and S2' whose phase rotations due to the static magnetic field non-uniformity are corrected can be obtained and an addition operation or subtraction operation of the above formulae (7) and (8) gives water image W(x,y) as an addition image or fat image F(x,y) as a subtraction image.

$$S1'(x,y)+S2'(x,y)=2W(x,y)$$

$$S1'(x,y)-S2'(x,y)=2F(x,y)$$

If the SE sequence is employed, since only the phase rotation starting from acquisition of S1 need be corrected, addition or subtraction of the image data S1 and the corrected S2' is performed to produce water/fat separated images.

Figure 10:
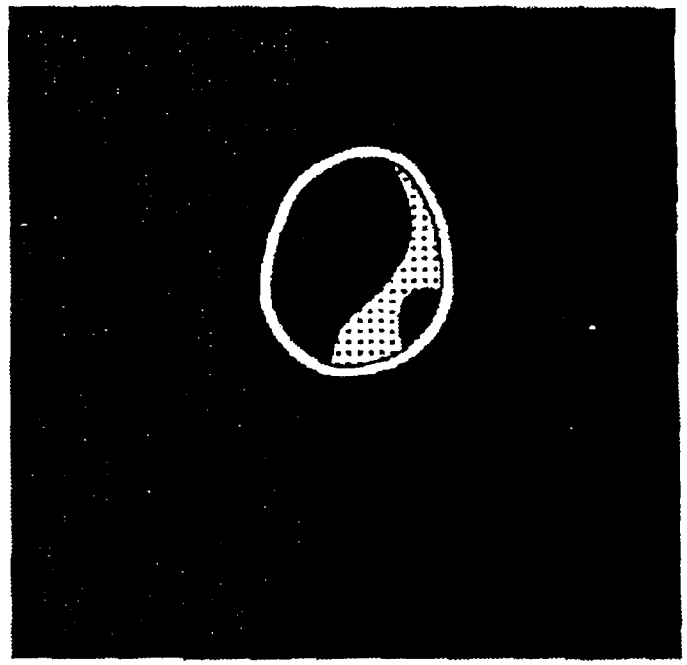
FIG. 10 shows an example of a fat-water separated image according to one embodiment of the present invention.
Figure 10:
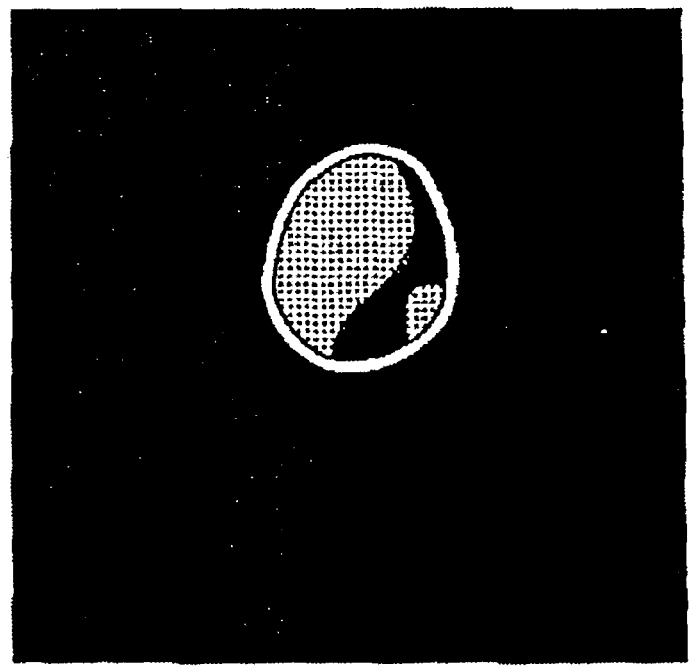

The thus obtained water image and fat image are displayed on the display 708. FIG. 10 illustrates an image obtained by performing the water/fat separation processing on the subject region indicated on the image 800 shown in FIG. 8. Here, (A) is a water-image and (B) is a fat-image. Either or both of the water image and fat image may be displayed. As for a portion other than the subject region, it is preferable for the non-processed image to be displayed at a lowered contrast because this clarifies how the water/fat separation processed portion is related to the whole image.

Figure 11:
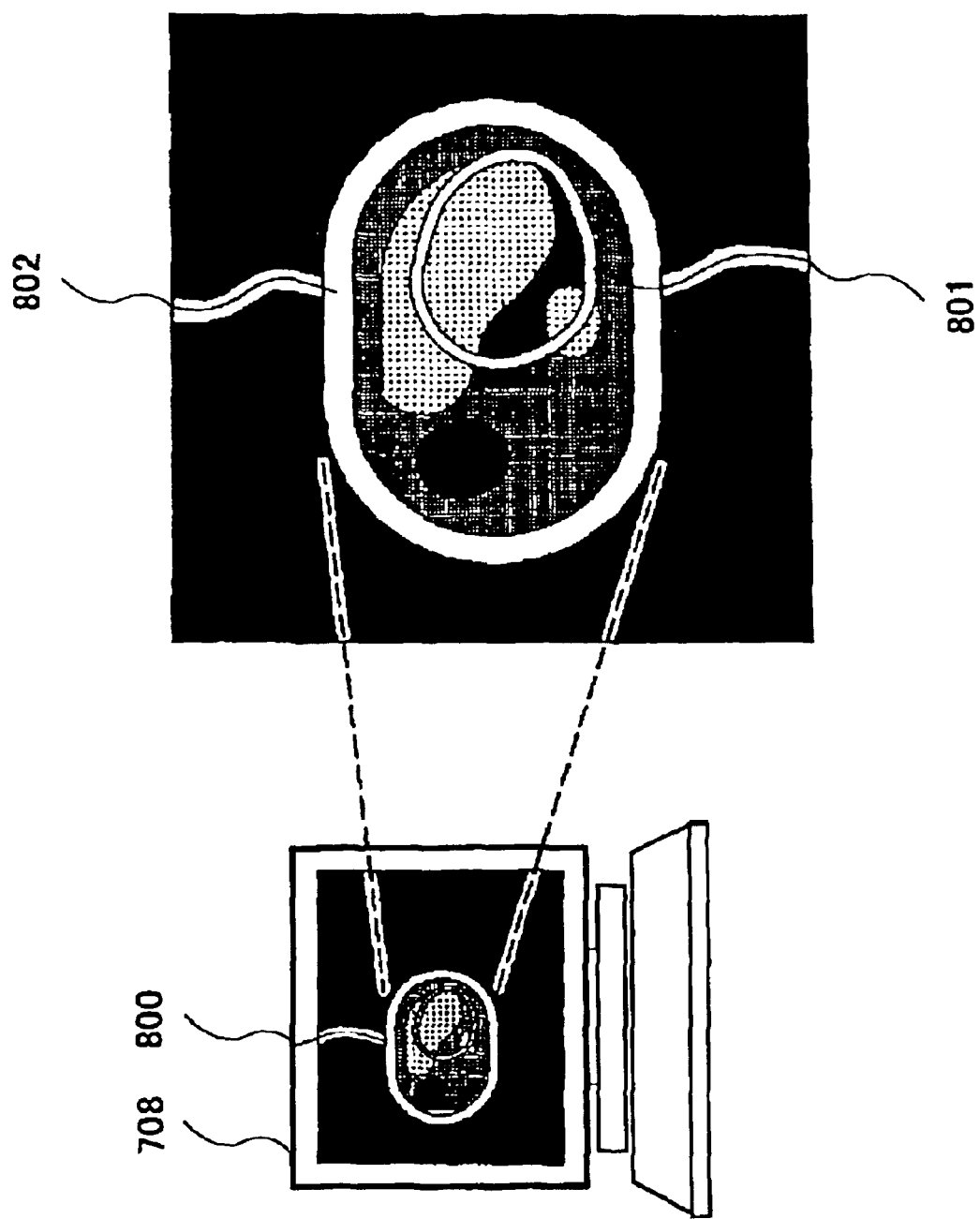
FIG. 11 shows another example of a fat-water separated image according to one embodiment of the present invention.
Figure 12:
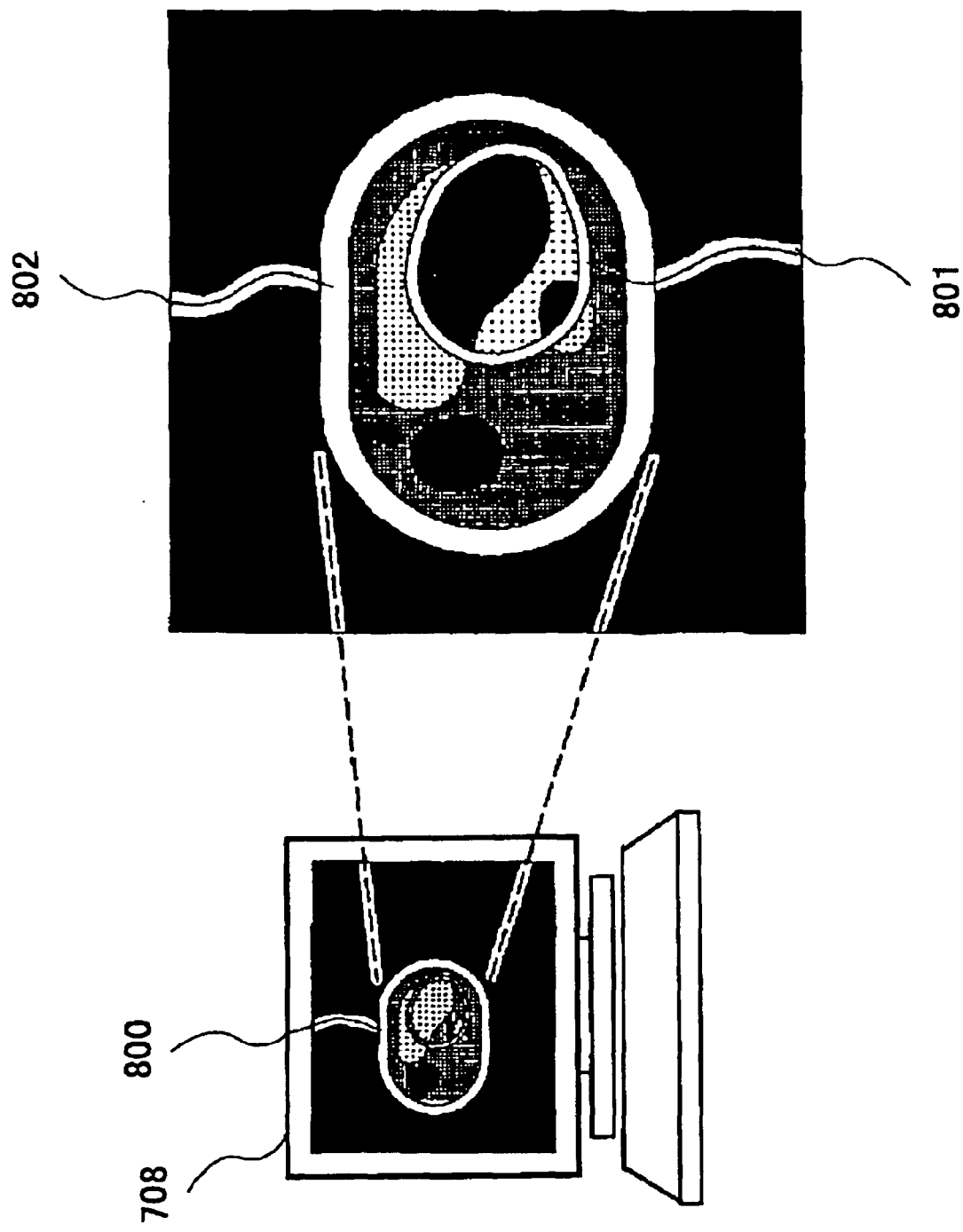
FIG. 12 shows another example of a fat-water separated image according to one embodiment of the present invention.

FIG. 11 and FIG. 12 illustrate examples of displayed images. In the examples shown in FIG. 11 and FIG. 12, a water/fat separation processed image, water image or fat image, is displayed for the indicated region 801 and a non-processed image is displayed for the region 802 other than the designated region. Specifically, in the example shown in FIG. 11, a water image is displayed in a region 801 of the original image 800, and image of the other portion 802 displays the image in the original state. In the example shown in FIG. 12, a fat image is displayed in a region 801 of the original image 800 and image of the other portion 802 displays the image in the original state.

By displaying the separation-processed image together with the original image, the position of the water/fat separation in the whole image can be recognized by a glance, and comparison of the water/fat processed region and the other portion is facilitated.

The imaging method according to the first embodiment of the present invention has been explained for the application to the 3PD method. The imaging method can be applied to the 2PD method similarly. The application of the present invention to the 2PD method accompanied by a static magnetic field correction now will be explained.

Figure 2:
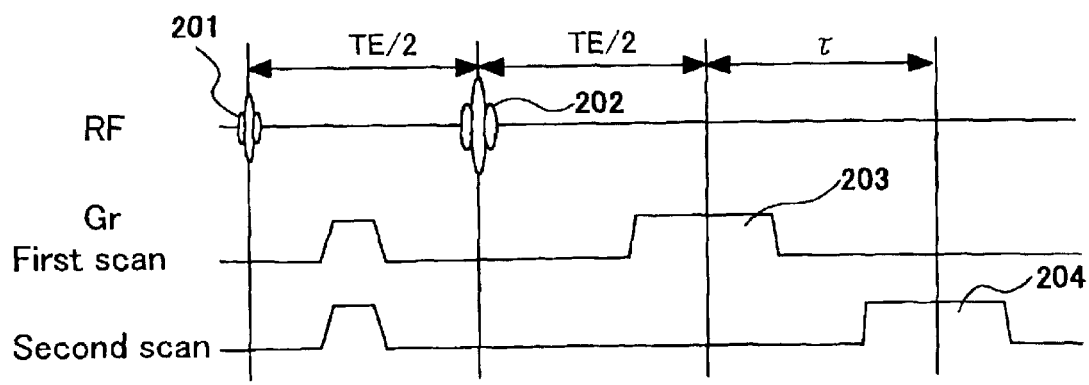
FIG. 2 is a time chart of data acquisition in the 2PD method using an SE sequence.

In this case, the measurement is performed using an SE sequence or GrE sequence similarly to the 3PD method. As shown in FIG. 1 and FIG. 2, the scan is conducted twice with the echo time TE set to different times TE1 and TE2. Alternatively, a multi-echo type SE or GrE sequence is conducted to generate two echoes within each repetition and the scan is conducted once. The measurement acquiring two echoes during a single scan reduces the measurement time, which is very beneficial for users.

In any case, the time difference between TE1 and TE2 is set to $(2n+1)\tau$ and, ordinarily TE2 is set to TE1+$\tau$.

The MR signals s1 and s2 thus obtained at different echo times TE1, TE2 are subjected to Fourier transform to produce image data S1 and S2. Since the image data S1 and S2 are complex data, absolute value (magnitude) images are displayed on the display 708. The images displayed here may be either or both of S1 and S2. Next, a user indicates a region to be water/fat separation-processed on the displayed image by drawing a border enclosing the region using a delineating tool such as a mouse pointer or pen.

Once the subject region has be designated, water/fat separated images are found only for the subject region according to the aforementioned 2PD method with a static magnetic field correction in the manner same as in the application to the 3PD method, and displayed on the display 708. Regarding the manner of displaying images, the subject region may be displayed alone or, preferably, together with the original image for the region other than the subject region as explained with respect to the 3PD method.

As previously mentioned, the 2PD method with a static magnetic field correction requires more complicated processing and a longer processing time than the 3PD method since it uses signals in which water spins and fat spins are out-phase. Accordingly, the measurement time reduction effect of the present invention is especially advantageous. The measurement time reduction effect brought about by the invention amounts to, for example, a reduction to about ¼ when the length of each side of a square subject region is ½ that of the original image.

The aforementioned imaging method according to the first embodiment can be applied to not only the measurement of a single image but also plural images obtained by dynamic imaging or multi-slice imaging.

Dynamic imaging is an imaging method where the same portion of the patient is measured at regular intervals to obtain a series of images showing change in the portion over the course of time. In case of dynamic imaging, a magnitude image obtained by the first scan is displayed, and a region to be water/fat separation processed is determined on the magnitude image. In the second and later scans, an image which is partially water/fat separation processed for the determined region is produced and displayed in real time.

In the conventional technique, since it takes a long time, 20 s–30 s, to perform the water/fat separation process, it is difficult to produce water/fat separated images corresponding to the acquired images one by one (i.e., real time images). However, the water/fat separation processing can be performed within several seconds by applying the imaging method of the present invention to the dynamic imaging, and water/fat separated images corresponding to the acquired images one by one can be produced.

While either of the 3PD method or 2PD method mentioned earlier may be employed for the dynamic imaging, the best real time characteristic can be obtained when a two-echo GrE sequence (2PD) having a short measurement time is employed.

In addition, the location of the inspection site may change during a time series of data is collected in the dynamic imaging. To cope with such a case, a design that enables the subject region to be reset and set through GUI as an occasion demands is preferable. By this, any movement of the inspection site can be easily dealt with.

A multi-slice imaging is a method which acquires MR signals from plural slices during one repetition time TR. In this case, an absolute image of one slice is displayed first and the subject region is determined on the displayed image. Then the determined region is used for all of the slices to perform the water/fat separation processing. Alternatively, the subject region may be determined for each slice. Since the water/fat separation processing is performed after the measurement, determination of the subject region can be done without time constraint and designed to be switched arbitrarily by the user.

As mentioned earlier, the first embodiment of the present invention is configured such that, in an MRI apparatus and method for obtaining water/fat separated images by acquiring a plurality of original image data having different echo times and performing operations on the original data, a partial region of the original image data is specified and the water/fat separation processing is performed for the specified region.

Since noise components included in the specified region are fewer than those included in the original image data, noise-induced errors in the processing operations, e.g., phase unwrap processing, can be reduced to suppress image degradation and enable production of improved-quality water/fat separated images.

In addition, since the data volume for the water/fat separation processing is reduced, the time required for the water/fat separation processing can be reduced. Accordingly, there can be provided an MI apparatus and method capable of producing water/fat separated images having improved image accuracy in a short processing time.

Next, a second embodiment of the present invention will be explained with reference to FIG. 13–FIG. 16.

This embodiment is characterized in that, when images such as water/fat separated images are produced by performing processing operations between plural images having different echo times, polarities of read-out gradient magnetic fields for generating echo signals having different echo times are equalized so that components not proportional to time are not appended to the individual echo signals, thereby improving image quality.

Figure 7:
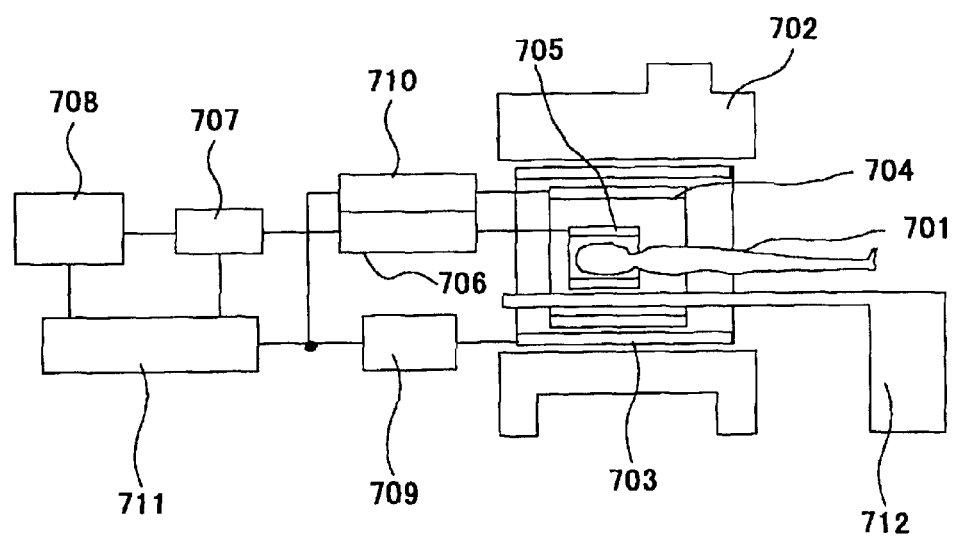
FIG. 7 is an overall diagram of an MRI apparatus to which the present invention can be applied.
Figure 6:
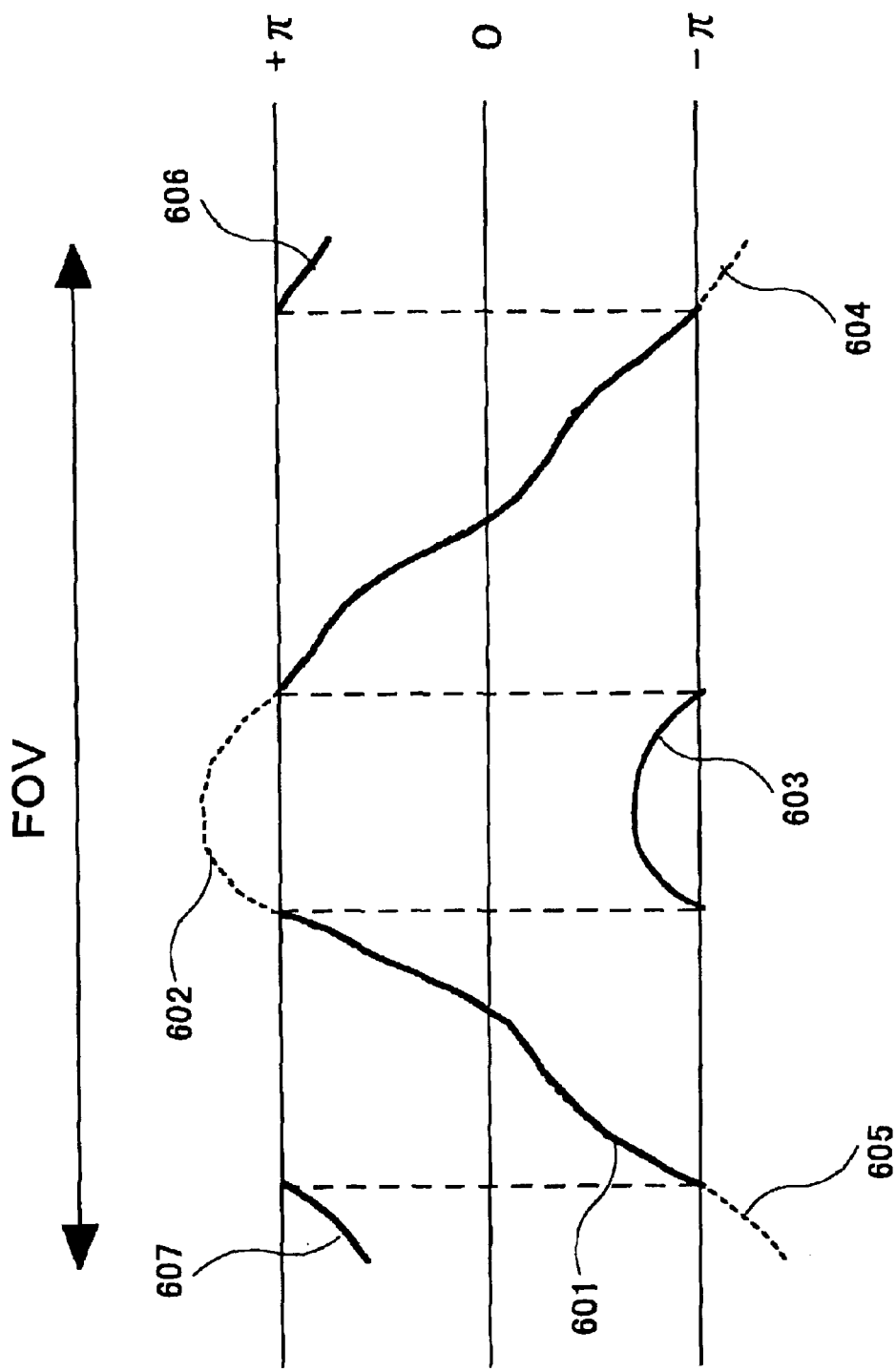
FIG. 6 shows a static magnetic field non-uniformity distribution within a FOV.

This embodiment is also applied to the MRI apparatus having an overall configuration as shown in FIG. 7. Here, however, a single-scan sequence of acquiring multiple echoes in a single scan is conducted, and the control unit 711 effects control such that the polarities of gradient magnetic fields for generating echo signals are equalized for echoes acquired in the scan.

Figure 13:
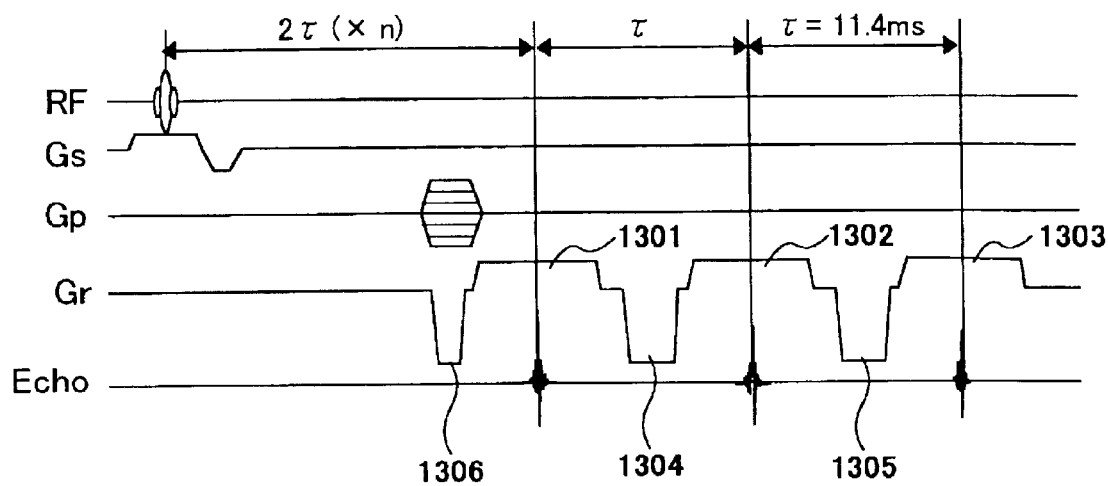
FIG. 13 shows a single-scan sequence (GrE sequence) of the 3PD method according to one embodiment of the present invention.

An application of the present invention employing a GrE type single scan sequence now will be explained hereinafter. According to this sequence, as shown in FIG. 13, an RF exciting pulse (RF) and a gradient magnetic field (Gs) are applied, and then a readout gradient magnetic field pulse (pre-pulse) 1306 is applied in the negative direction. Thereafter a readout gradient magnetic field pulse 1301 is applied in the positive direction to generate a first echo signal 2τ after application of the RF exciting pulse. Next, a second echo signal is generated τ after generation of the first echo signal by applying a readout gradient magnetic field pulse rewind pulse) 1304 in the negative direction and a readout gradient magnetic field pulse 1302. Finally, a gradient magnetic field pulse (rewind pulse) 1305 in the negative direction and a readout gradient magnetic field 1303 are applied to generate a third echo signal τ after the generation of the second echo signal. The application of the RF exciting pulse and gradient magnetic fields is repeated plural times (for example 256 times) while changing the phase encode to produce three kinds of image data having different echo times. By thus applying the rewind pulses 1302, 1305, the polarities of the readout gradient magnetic fields 1301, 1302, 1303 for generation of echo signals can be equalized.

The application times of the readout gradient magnetic fields 1301, 1302, 1303 can be longer in proportion as the intensities of the gradient magnetic fields for these rewind pulses are larger and the application times are shorter. Therefore, the receiving bandwidth can be narrowed and the SN ratio can improved. Accordingly, it is preferred to make the pulse intensities of the pre-pulse 1306 and rewind pulses 1304, 1305 high and to make the pulse widths narrow.

The rewind pulses 1304, 1305 have polarities opposite to the readout gradient magnetic fields 1302, 1303 and the same area as the readout gradient magnetic fields 1302, 1303. The pre-pulse 1306 has the same polarity and the same intensity as the readout gradient magnetic field 1304 but a half pulse width. So far as these relationships are maintained, the polarities shown in the figure may be reversed, i.e., the pre-pulse 1306 and rewind pulses 1304, 1305 may be applied in the positive direction and the readout gradient magnetic fields 1301, 1302, 1303 may be applied in the negative direction.

Next, another application of the present invention employing an SE type single scan sequence will be explained with reference to FIG. 14. In this case, an RF exciting pulse and a slice gradient magnetic field are applied and then an inversion RF pulse is applied at ½ echo time. Then, after a gradient magnetic field (pre-pulse) 1406 is applied, a readout gradient magnetic field 1401 is applied in the positive direction to generate a first echo signal TE after application of the RF exciting pulse. Next, gradient magnetic field rewind pulse) 1404 in the negative direction and a readout gradient magnetic field 1402 are applied again to generate a second echo signal τ after generation of the first echo signal. Finally, a readout gradient magnetic field (rewind pulse) 1405 in the negative direction and a readout gradient magnetic field 1403 are applied to generate a third echo signal τ after generation of the second echo signal. The application of the RF exciting pulse and gradient magnetic fields is repeated plural times (for example 256 times) while changing phase encode to produce three kinds of image data having different echo times.

By applying the rewind pulses 1404 and 1405, the polarities of the readout gradient magnetic fields 1401, 1402, 1403 for generation of echo signals can be equalized, similarly to the application to the GrE type single-scan sequence.

Similarly to the previous embodiment, so far as the rewind pulses 1404 and 1405 have polarities opposite to and areas equal to the readout gradient magnetic fields 1302 and 1303, and the pre-pulse 1306 has a polarity and intensity equal to the readout gradient magnetic field 1304 but a half pulse width, the pre-pulse 1406 and rewind pulses 1404, 1405 may be applied in the positive direction and the readout gradient magnetic fields 1401, 1402, 1403 may be applied in the negative direction.

By equalizing the polarities of the readout gradient magnetic fields 1301–1303 and 1401–1403, influence of eddy currents caused by inversion of a gradient magnetic field can be suppressed. This enhances the accuracy of the water/fat separation processing to produce excellent water/fat separated images.

Figure 14:
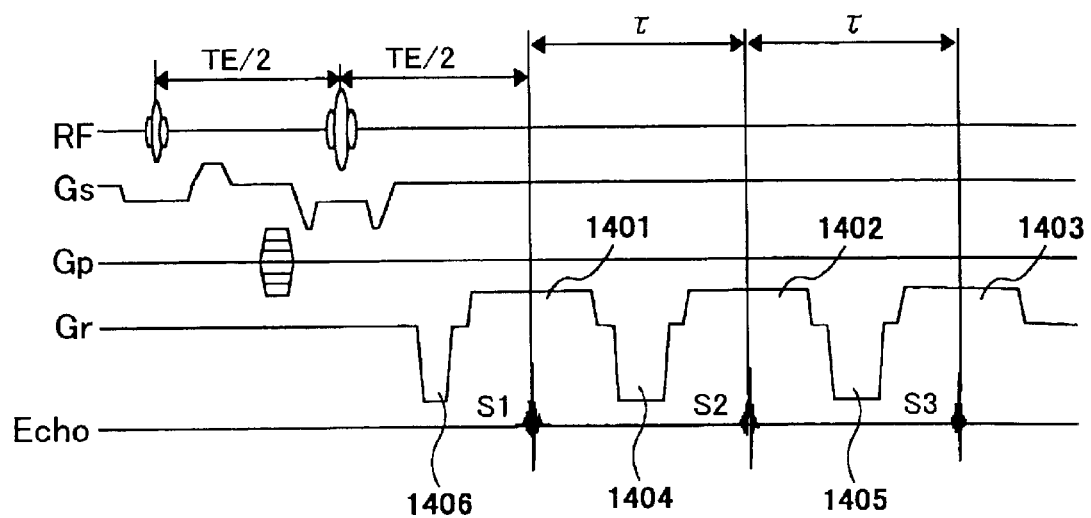
FIG. 14 shows a single-scan sequence (SE sequence) of the 3PD method according to one embodiment of the present invention.

In FIG. 13 and FIG. 14, water signals and fat signals in the first echo are in phase (same phase), out of phase (different phase) in the second echo and in phase in the third echo. Since the second echo is out of phase, water signals and fat signals cancel each other so that signal intensity is lowered in a portion where water and fat co-exist. On the other hand, since the first and third echoes are in phase, the signals can have high intensity without canceling each other even in a portion where water and fat co-exist. Accordingly, when the static magnetic field non-uniformity map is formed using the first echo and third echo, an accurate static magnetic field non-uniformity map can be produced even in a portion where water and fat co-exist. This is very important for obtaining water/fat separated image stably. According to an investigation conducted by the inventors, stable water/fat images could be obtained even if the first echo was slightly out of phase (about $\pi/10$ shifted from the in-phase state) and such a shift was tolerable.

The first to third echoes may be acquired as out-of phase, in-phase and out-of phase echoes by properly determining the acquisition time of the first echo from the RF exciting pulse or RF inversion pulse. In this case, too, influence of eddy currents caused by inversion of a gradient magnetic field can be suppressed. However, an experiment conducted by the inventors showed that acquisition of echoes in the order of in-phase, out-of-phase and in-phase resulted in more stable processing and was effective.

The value of $\tau$ in FIG. 13 and FIG. 14 is expressed by $1/2\gamma\sigma B$ ($\tau=1/2\gamma\sigma B$) using the relations of $\Delta f=\gamma\sigma B$ ($\sigma$ is the chemical shift difference between water and fat) and $2\tau=1/\Delta f$, which decreases in inverse proportion to the static magnetic field intensity. Accordingly, this embodiment is more suitable for the middle or low magnetic field class MRI apparatus than for the high magnetic field class MRI apparatus. Typically, the embodiment is easily realized in the static magnetic field intensity of 0.2T–0.5T, especially about 0.3T. If the technique of the present invention is applied to an MRI apparatus of 0.3T, $\tau$ will be 11.4 m. If the magnetic field intensity becomes high and $\tau$ becomes short, the rise time and fall time of the gradient magnetic field pulse increase relatively and the time of signal acquisition is shortened. In order to collect required data during the measurement time, it is necessary to shorten the sampling interval. As a result, the receiving bandwidth becomes wide and the S/N becomes low. In order to shorten the rise time and fall time of the gradient magnetic field, the rising characteristic of the gradient magnetic field should be improved.

The inventors conducted an experiment on water/fat separation according to this embodiment of the present invention using a 0.3T open-type MRI apparatus. The apparatus was equipped with a permanent magnet and pole pieces for generating the static magnetic field, and had a vertical magnetic field system and an asymmetrical two-post structure. The slew rate of the gradient magnetic field was 20T/m/s. In the imaging sequence of the experimental imaging, both of the rise time and fall time of the readout gradient magnetic field was 850 μs. The signal detecting band was 35 kHz (FOV=350 mm) or 45 kHz (FOV=200m) and the matrix size was 256×256. Under such imaging conditions, imaging according to the embodiment was realized easily.

Use of rewind pulses in an echo planar imaging (EPI) using a high magnetic field MRI is described in "Echo-Planar Imaging with Asymmetric Gradient Modulation and Inner-Volume Excitation"; D. A. Feinberg et al.; Magnetic Resonance in Medicine, Vol. 13, 162–169 (1990). EPI is also susceptible to the phase rotation caused by inversion of a readout gradient magnetic field. However, in EPI, plural echo signals having different echo times are differently phase-encoded in order to produce one image quickly. The imaging of the present invention is different from the EPI in that echo signals having different echo times are acquired to collect echo signals having the same echo time of a number equal to a repetition number and to produce three images. It is also different in that echo signals having different echo times generated in the same TR are imparted with the same phase-encode. Yet, effect of the rewind pulse is different. Specifically, in the embodiment of the present invention, the rewind pulse is used for matching between three images having different characteristics, whereas the rewind pulse is used for matching between signals of one image in EPI. Accordingly, the embodiment is not a simple application of the rewind pulse of EPI.

A technique of producing water/fat separated images from in-phase, out-of-phase and in-phase data in a single scan sequence is disclosed in "Separation of water and fat MR images in a single scan at 0.35 T using "Sandwich" echoes", W. Zhang et al., Journal of Magnetic Resonance Imaging, Vol. 6, no. 6, PP 909–917, 1996. Although this article discloses inversion of the polarities of the first and third echoes, it does not disclose that polarities of all of echo signals are equalized as in the present embodiment.

Another embodiment of the present invention now will be explained. In this embodiment, the sequences shown in FIG. 13 and FIG. 14 are modified so that influence of readout gradient magnetic fields applied at acquisition of echo signals is equalized for the first echo, second echo and third echo. In the following figure, the same symbols as in FIG. 13 and FIG. 14 are used for the same components.

Figure 15:
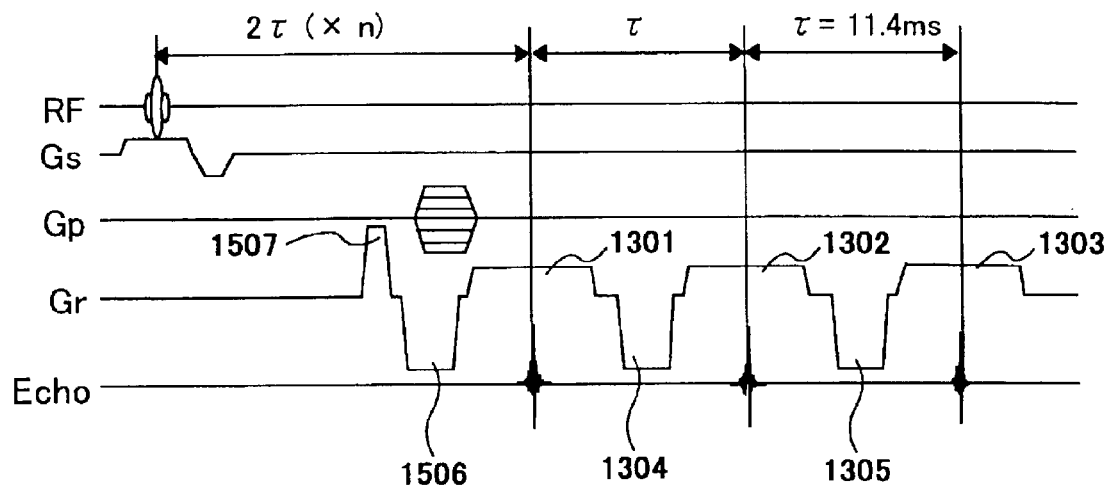
FIG. 15 shows a single-scan sequence (GrE sequence) of the 3PD method according to another embodiment of the present invention.

One application employing a GrE type single scan sequence is illustrated in FIG. 15. In the sequence shown in FIG. 15, a rewind pulse 1506 having an application time and intensity equal to the rewind pulses 1304, 1305 is applied instead of the pre-pulse 1306 of FIG. 13, and a pre-pulse having a polarity opposite to the rewind pulse 1506 and a half pulse area is added ahead of the rewind pulse 1506. By applying the pre-pulse 1507, a half area of the rewind pulse 1506 is offset and, as a result, readout gradient magnetic fields 1301, 1302 and 1303 can be applied in the same polarity similarly to the sequence shown in FIG. 13. In addition, since the intensity and application time of the rewind pulses 1304, 1305 and 1506 are equalized by applying the pre-pulse 1507, influence of readout gradient magnetic fields applied at acquisition of echoes, i.e., influence of eddy currents caused by inversion of the polarity of the gradient magnetic field, is equalized for the first echo, second echo and third echo.

Figure 16:
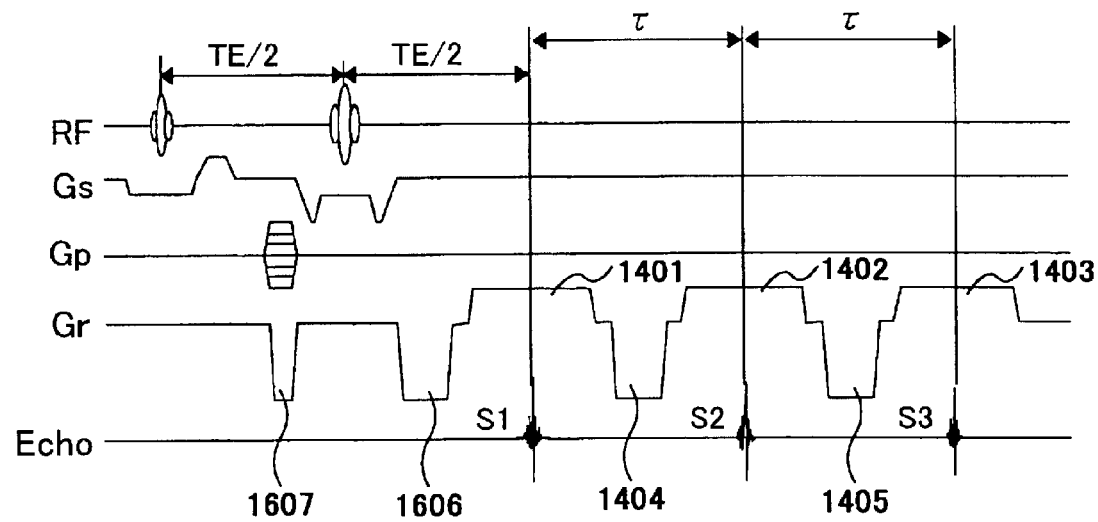
FIG. 16 shows a single-scan sequence (SE sequence) of the 3PD method according to another embodiment of the present invention.

Another application using an SE type single scan sequence is shown in FIG. 16. In the sequence of FIG. 16, a rewind pulse 1606 having a longer application time is applied instead of the pre-pulse 1406 of FIG. 14, and a pulse 1607 having the same polarity as the rewind pulse 1606 and a half area is added ahead of the rewind pulse 1606. This makes it possible not only to apply readout gradient magnetic fields 1401, 1402, 1403 with the same polarity but also to equalize the intensity and application time of the rewind pulses 1606, 1404 and 1405. Similarly to the aforementioned GrE type, influence of readout gradient magnetic fields applied at acquisition of echoes, i.e., influence of eddy currents caused by inversion of the polarity of gradient magnetic fields, is equalized for the first echo, second echo and third echo.

Specifically, in the embodiments of FIG. 13 and FIG. 14, although the application time and intensity of readout gradient magnetic fields 1301–1303, 1401–1403 are the same for the first echo, second echo and third echo, pulses applied ahead of them (pre-pulses 1306, 1406 and rewind pulses 1304, 1305, 1404, 1405) are not identical and image degradation might occur owing to disturbance of phase rotation components due to application of the thus different gradient magnetic fields. However, if the pulses applied ahead of the readout gradient magnetic fields 1301–1303, 1401–1403 are equalized as aforementioned, such problem can be solved.

Since the polarities of all of the readout gradient magnetic field 1301–1303, 1401–1403 are equalized and the application times and intensities of the readout gradient magnetic field 1301–1303, 1401–1403 which are applied ahead of the rewind pulses 1506, 1304, 1305, 1606, 1404, 1405 are equalized, disturbance owing to the influence of application of gradient magnetic fields for the first-third echoes can be suppressed. Since influence of eddy currents caused by inversion of gradient magnetic fields and disturbance thereof can be thus suppressed, accurate water/fat separation processing can be done to produce excellent water/fat separated images.

In FIG. 15, the height of the pre-pulse 1507 may be lower than that of the rewind pulse 1506. Similarly, in FIG. 16, the height of the pre-pulse 1607 may be lower than that of the rewind pulse 1606. If the height of a pulse is lowered, the pulse area is maintained the predetermined value by prolonging the application time.

Further, application of the pre-pulse 1607 ahead of the second RF pulse in FIG. 16 is effective for shortening TE. The reason is that, although the pre-pulse 1607 can be applied after the second RF pulse as a sequence design, reduction of TE is restrained in this case because two pulses including the pre-pulse 1607 and the rewind pulse 1606 are applied during the last half of TE (TE/2). In addition, it becomes necessary to apply the pre-pulse with a reversed polarity.

In FIG. 13–FIG. 16, it is preferable to make the height of the rewind pulses 1304, 1305, 1404, 1405, 1506 and 1606 as high as possible. For example, in an MRI apparatus implemented with a gradient magnetic field system of the maximum gradient magnetic field of 15 mT/m, it may be more than about 14 mT/m. As a result, the application time of the readout gradient magnetic fields 1301–1303 and 1401–1403 can be long, the receiving bandwidth can be narrow and the image S/N can be improved.

The embodiments shown in FIG. 13–FIG. 16 are effective especially in an MRI apparatus influenced considerably by eddy currents generated by application of gradient magnetic fields, e.g., an MRI apparatus equipped with pole pieces having a large residual magnetic field and eddy currents.

The second embodiment applied to the Dixon method has been explained in the foregoing. This embodiment can be applied to imaging methods other than the Dixon method. Typical of these imaging methods is the method of Qing-San Xiang et al., in which plural image data having different TE are acquired, and water signals and fat signals are separated by performing processing operations on the acquired image data to produce images. Further, this embodiment can be applied to not only separation of water signals and fat signals but also to procession operations on plural image data having different TE to improve precision of the operations.

According to the second embodiment, when plural image data having different echo times are acquired, components not proportional to time can be eliminated from each echo. This makes it possible to accurately implement a method of water/fat separation imaging by processing operations and to produce excellent water/fat-separated images.

What is claimed is:

1. A magnetic resonance imaging method of producing water/fat-separated images by acquiring original image data of plural images having different echo times and performing processing operations thereon, which method includes the steps of specifying a partial region of the original image data to be subjected to water/fat separation processing operations and performing the water/fat separation processing operations on the specified region to produce water images or fat images thereof.

2. The magnetic resonance imaging method of claim 1, wherein the acquired original image data having different echo times consist of image data of at least two images.

3. The magnetic resonance imaging method of claim 1, wherein a plurality of regions can be specified for the water/fat separation processing.

4. The magnetic resonance imaging method of claim 1, which method further includes the steps of displaying the original image on a display means, specifying the partial region for perform the water/fat separation processing through the displayed original image, displaying a water/fat-separated image for the specified region and a non-processed image for a region other than the specified region.

5. The magnetic resonance imaging method of any one of claims 1–3, wherein acquisition of the original image data is conducted continuously and the water/fat-separated image is displayed and updated in real time.

6. The magnetic resonance imaging method of claim 5, wherein the step of specifying of the partial region for the water/fat separation processing is conducted at arbitrary time during continuous acquisition of the original image data.

7. A magnetic resonance imaging apparatus comprising a signal detecting unit for detecting NMR signals emitted from a subject to be examined, a signal processing unit for performing image processing on the detected signals, a display unit for displaying the signal-processed images, a control unit for controlling operations of the signal detecting unit, the signal processing unit and the display unit, and producing water/fat-separated images by acquiring plural original image data of plural images having different echo times and performing processing operations thereon, wherein a partial region of the original image data for performing the water/fat separation operation is specified through the display unit and is subjected to the water/fat separation processing operations by the signal processing unit, and the water/fat separation processed water images or fat images are displayed on the display unit.

8. A magnetic resonance imaging apparatus comprising a signal detecting unit for detecting NMR signals emitted from a subject to be examined, a signal processing unit for performing image processing on the detected signals, a display unit for displaying the signal-processed images, a control unit for controlling operations of the signal detecting unit, the signal processing unit and the display unit, and producing water/fat-separated images by acquiring original image data of plural images having different echo times and performing processing operations thereon, which apparatus further comprises means for specifying one or plural regions for performing the water/fat separation processing, wherein the signal processing unit performs the water/fat separation processing on the region selected by the specifying means and the display unit displays the processed water images or fat images.

9. The magnetic resonance imaging apparatus of claim 8, wherein the display means displays the water images or fat images superimposed on the original images.

10. A magnetic resonance imaging apparatus for producing images by acquiring plural images having different echo times by a single scan measurement and performing processing operations thereon, wherein the readout gradient magnetic fields with the same polarity are applied for acquiring echo signals having different echo times.

11. The magnetic resonance imaging apparatus of claim 10, wherein a rewind pulse having a polarity opposite to that of the readout gradient magnetic field is applied ahead of the readout gradient magnetic field.

12. A magnetic resonance imaging apparatus comprising means for generating a static magnetic field in a space where a subject to be examined is placed, means for repeatedly applying an RF pulse to produce NMR in the subject, means for applying gradient magnetic fields in the slice direction, in the phase encode direction and in the readout direction, receiving means for detecting plural echo signals emitted from the subject, control means for controlling the said means such that plural echo signals are generated at different echo times during each RF pulse repetition time by applying readout gradient magnetic fields while changing phase encode at each repetition, and processing means for producing images by performing processing operations on the echo signals having different echo times, wherein the control means effects control such that a pulse with a polarity opposite to the readout gradient magnetic field is applied ahead of the readout gradient magnetic field.

13. The magnetic resonance imaging apparatus of claim 12, wherein the control means effects control such that the pulse is applied ahead of readout gradient magnetic fields for the second and subsequent echo signals in each repetition time.

14. The magnetic resonance imaging apparatus of claim 12, wherein the control means effects control such that the pulse is applied ahead of readout gradient magnetic fields for every echo signals.

15. A magnetic resonance imaging apparatus for producing images by acquiring plural images having different echo times by a single scan measurement and performing processing operations thereon, wherein the readout gradient magnetic field with the same polarity is applied for acquiring each of temporally adjacent echo signals.

* * * * *